United States Patent [19]

Balzarini

[11] Patent Number: 5,968,910
[45] Date of Patent: Oct. 19, 1999

[54] COMPOSITIONS CONTAINING TWO OR THREE INHIBITORS OF DIFFERENT HIV REVERSE TRANSCRIPTASES

[75] Inventor: Jan Maria René Balzarini, Heverlee, Belgium

[73] Assignee: Jan M. R. Balzarini, Heverlee, Belgium

[21] Appl. No.: 08/346,721

[22] Filed: Nov. 30, 1994

[51] Int. Cl.⁶ .................................................. A61K 31/70
[52] U.S. Cl. ................................ 514/45; 514/46; 514/49; 514/50; 514/448; 514/471; 536/27.6; 536/27.8; 536/27.81; 536/28.4; 536/28.5; 536/28.51; 536/28.52; 536/28.53; 536/28.54; 536/28.55; 536/28.7; 549/71; 549/506
[58] Field of Search ................................ 514/45, 46, 49, 514/50, 448, 471; 536/27.6, 27.8, 27.81, 28.4, 28.5, 28.51, 28.52, 28.53, 28.54, 28.55, 28.7; 549/71, 506

[56] References Cited

U.S. PATENT DOCUMENTS 5,268,389  12/1993  Harrison .................................. 514/485

FOREIGN PATENT DOCUMENTS

| 0484071 | 5/1992 | European Pat. Off. . |
| 0530407 | 3/1993 | European Pat. Off. . |
| 9105761 | 5/1991 | WIPO . |

OTHER PUBLICATIONS

Balzarini et al, "2',5'-Bis-O-(tert-butyldimethylsilyl)-3'-spiro-5"-(4"-amino-1",2"-oxathiole-2",2"-dioxide)pyrimidine (TSAO) nucleoside analogues: Highly selective inhibitors of human immunodeficiency virus type 1 that are targeted at the viral reverse transcriptase", Proc. Natl. Acad. Sci. USA, 89: 4392–4396 (May 1992).

Camarasa et al, "3'-Spiro Nucleosides, a new Class of Specific Human Immunodeficiency Virus Type 1 Inhibitors: Synthesis and Antiviral Activity of [2', 5'-Bis-O-(tert-butyldimethylsilyl)-β-D-xylo-and -ribofuranose]-3'-spiro-5"-(4"-amino-1",2"-oxathiole-2", 2"-Dioxide)(TSAO)Pyrimidine Nucleosides", J. Med. Chem. 35: 2721–2727 (1992).

Perez–Perez et al, "TSAO analogues. Stereospecific Synthesis and Anti–HIV–1 Activity of 1–[2', 5'-Bis-O-(tert-butyldimethylsilyl)-β-D-ribofuranosyl]-3'-spiro-5"-(4"-amino-1",2"-oxathiole-2", 2"-dioxide)Pyrimidine and Pyrimidine-Modified Nucleosides", J. Med. Chem., 35: 2988–2995 (1992).

Balzarini et al, "Treatment of Human Immunodeficiency Virus Type 1 (HIV–1)–Infected Cells with Combination of HIV–1–Specific Inhibitors Results in a Different Resistance Pattern Than Does Treatment with Single–Drug Therapy", J. Virol., 67(9): 5353–5359 (Sep. 1993).

Balzarini et al, "HIV–1–Specific Reverse Transcriptase Inhibitors Show Differential Activity against HIV–1 Mutant Strains Containing Different Amino Acid Substitutions in the Reverse Transcriptase", Virology, 192: 246–253 (1993).

Balzarini et al, "TSAO derivatives: highly specific human immunodeficiency virus type 1 (HIV–1) reverse transcriptase inhibitors", Drugs of the Future 1993, 18(11): 1043–1055.

Velázquez et al., TSAO Analogues. 3. Synthesis and Anti–HIV–1 Activity of 2',5'-Bis-O-(tert-Butyldimethylsilyl)-β-D-ribofuranosyl 3'-Spiro-5"-(4"-amino-1",2"-oxathiole 2",2"-dioxide) Purine and Purine–Modified Nucleosides, J. Medicinal Chem., 36(22), 3230–3239 (1993).

Balzarini et al.(I), "Knocking–Out Concentration of HIV–1–Specific Inhibitors Completely Suppress HIV–1 Infection and Prevent the Emergence of Drug–Resistant Virus," Virology, 196(2), 576–585 (1993).

Balzarini et al. (II), "Human Immunodeficiency Virus Type 1 (HIV–1) Strains Selected for Resistance Against the HIV–1–Specific [2',5'-Bis-O-(tert-Butyldimethylsilyl)-3'-spiro-5"-(4"-amino-1",2"-oxathiole-2",2"-dioxide)]-β-D-pentofuranosyl (TSAO) Nucleoside Analogues Retain Sensitivity to HIV–1–Specific Non-nucleoside Inhibitors," Proc. Nat. Acad. Sci. USA, 90(15), 6952–6956 (1993).

Balzarini et al (III), "Kinetics of Inhibition of Human Immunodeficiency Virus Type 1 (HIV–1) Reverse Transcriptase by the Novel HIV–1–Specific Nucleoside Analogue [2', 5'-Bis-O-(tert-Butyldimethylsilyl)-β-D-ribofuranosyl]-3'-spiro-5"-(4"-amino-1",2"-oxathiole-2", 2"-dioxide)thymine (TSAO-T)," J. Biol. Chem., 267(17), 11831–11838 (1992).

Balzarini et al. (IV), "[2', 5'-Bis-O-(tert-Butyldimethylsilyl)]-3'-spiro-5"-(4"-amino-1",2"-oxathiole-2",2"-dioxide) (TSAO) Derivatives of Purine and Pyrimidine Nucleosides as Potent and Selective Inhibitors of Human Immunodeficiency Virus Type 1," Antimicrobial Agents and Chemotherapy, 36(5), 1073–1080 (1992).

Balzarini et al. (V), "Supression of the Breakthrough of Human Immunodeficiency Virus Type 1 (HIV–1) in Cell Culture by Thiocarboxanilide Derivatives When Used Individually or in Combination with Other HIV–1–Specific Inhibitors (i.e. TSAO Derivatives)," Proc. Nat. Acad. Sci. USA, 92(12), 5470–5474 (1995).

E. De Clercq, "Non–nucleoside reverse transcriptase inhibitors (NNRTIs)", Exp. Opin. Invest. Drugs 3(3): 253–271 (1994) (Mar.).

(List continued on next page.)

*Primary Examiner*—John Kight
*Assistant Examiner*—L. Eric Crane
*Attorney, Agent, or Firm*—Daniel Reitenbach

[57] ABSTRACT

A composition and method for the prevention or treatment of HIV-1 infection comprising an HIV-1 reverse transcriptase-inhibiting heterocyclyl carb(ox/thio)anilide compound, a second HIV-1 reverse transcriptase inhibitor compound which does not select for the same HIV-1 mutant strain or strains selected for by the heterocyclyl carb(ox/thio)anilide compound, and, optionally, a third HIV reverse transcriptase inhibitor compound.

18 Claims, No Drawings

OTHER PUBLICATIONS

E. De Clercq, "Resistance of Human Immunodeficiency Virus Type 1 (HIV–1) to Non–nucleoside HIV–1 Specific Reverse Transcriptase Inhibitors", Int. J. Immunotherapy X(4): 145–158 (1994).

Kilby et al, "Is There a role for Non–nucleoside Reverse Transcriptase Inhibitors in the Treatment of HIV Infection?", Infectious Agents and Disease 3(6): 313–323 (1994).

D. L. Romero, "Delavirdine Mesylate", Drugs of the Future 19(3): 238–242 (1994).

M. A. Fischl, "Combination Antiretroviral Therapy for HIV Infection", Hospital Practice: 43–48 (Jan. 15, 1994).

T. B. Campbell, "New antiretroviral agents for the therapy of HIV type–1 infection", Current Opinion in Infectious Diseases 6: 768–772 (1993) Dec.

COMPOSITIONS CONTAINING TWO OR THREE INHIBITORS OF DIFFERENT HIV REVERSE TRANSCRIPTASES

FIELD OF THE INVENTION

This invention relates to a composition for the prevention or treatment of HIV-1 infection. More particularly, this invention relates to a composition for the prevention and/or treatment of HIV-1 infection which comprises, as active ingredients, an HIV-1 reverse transcriptase-inhibiting heterocyclyl carb(ox/thio)anilide compound, a second HIV-1 reverse transcriptase (RT) inhibitor compound, such as a 2',5'-bis-O-(tert-butyldimethylsilyl)-3'-spiro-5"-(4"-amino-1",2"-oxathiole-2",2"-dioxide)(TSAO) derivative, which does not select for the same HIV-1 mutant strain or strains selected for by the heterocyclyl carb(ox/thio)anilide compound, and, optionally, a third HIV reverse transcriptase inhibitor. This invention also relates to a method for the prevention or treatment of HIV-1 infection in a patient which comprises administering to the patient an effective amount of an HIV-1 RT inhibiting heterocyclyl carb(ox/thio)anilide compound, a second HIV-1 RT inhibitor compound which does not select for the same HIV-1 mutant strain or strains selected for by the heterocyclyl carb(ox/thio)anilide compound, and, optionally, a third HIV RT inhibitor compound.

BACKGROUND OF THE INVENTION

Various compounds have been described as inhibitors of human immunodeficiency virus type 1 (HIV-1) in vitro and are targeted at the virus-encoded reverse transcriptase (RT), e.g., nevirapine, pyridinone, TIBO, BHAP, TSAO, and quinoxaline. The selectivity of these compounds for HIV-1 is due to a highly specific interaction with HIV-1 RT.

The rapid emergence of HIV-1 strains resistant to several HIV-1-specific RT inhibitors in cell culture and in AIDS patients has caused concern for further development of these inhibitors in the clinic. However, HIV-1 resistance to one HIV-1-specific RT inhibitor does not necessarily imply cross-resistance to other HIV-1-specific RT inhibitors. Indeed, it has been proven that HIV-1-specific RT inhibitors show differential activity against HIV-1 mutant strains containing different amino acid substitutions in their RT. For example, HIV-1 strains containing the 100 Leu→Ile mutation in their RT are resistant to TIBO R82913 and R82150 but not to nevirapine and the TSAO derivatives TSAO-T and TSAO-m³T. Also, HIV-1 strains containing the 138 Glu→Lys mutation in their RT are resistant to TSAO derivatives but not to the other HIV-1-specific RT inhibitors, such as BHAP and nevirapine. In contrast, the 181 Tyr→Cys mutation in the RT of HIV-1 strains renders the mutant viruses resistant to virtually all HIV-1 specific RT inhibitors described to date except certain oxathiin carboxanilide derivatives described in U.S. Pat. No. 5,268,239. See, e.g., Balzarini et al, J. Virology 67(9): 5353–5359 (1993) ("Balzarini I") and Balzarini et al, Virology 192: 246–253 (1993) ("Balzarini II").

Unsuccessful attempts have been made to combine various HIV-1 RT inhibitors to eliminate virus resistance. See, e.g., Balzarini I.

Accordingly, it is the purpose of this invention to provide a composition comprising a combination of certain HIV RT inhibitor compounds which can inhibit or suppress the emergence of drug-resistant HIV-1 strains.

It is also the purpose of this invention to provide a method of preventing or treating HIV-1 infections by administration of this combination of certain HIV RT inhibitor compounds.

SUMMARY OF THE INVENTION

This invention relates to a composition for the prevention or treatment of HIV-1 infections which comprises a therapeutically effective amount of:

a) a first HIV-1 RT inhibitor compound of the formula

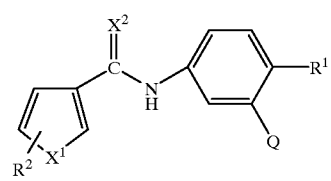

(I)

wherein $X^1$ and $X^2$ are independently O or S;

Q is

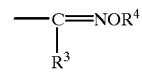

or $COYR^5$;

Y is O or S;

$R^1$ is hydrogen, halogen, $C_1$–$C_4$ alkyl, $C_1$–$C_4$ alkoxy, $C_3$–$C_4$ alkenyloxy, $C_3$–$C_4$ alkynyloxy, mono-, di- or trihalomethyl, trifluoromethoxy, $C_1$–$C_4$ alkylthio, $C_3$–$C_4$ branched alkylthio, nitro, or cyano;

$R^2$ is hydrogen, $C_1$–$C_4$ alkyl or halogen;

$R^3$ is hydrogen or $C_1$–$C_4$ alkyl;

$R^4$ is $C_3$–$C_6$ alkyl, $C_3$–$C_6$ alkenyl, $C_3$–$C_6$ alkynyl, $C_1$–$C_8$ haloalkyl, $C_1$–$C_8$ alkoxyalkyl, $C_1$–$C_8$ alkylthioalkyl, $C_1$–$C_8$ hydroxyalkyl, $C_1$–$C_8$ acyloxyalkyl, $C_1$–$C_8$ aroyloxyalkyl, $C_1$–$C_8$ carboxyalkyl, $C_1$–$C_8$ alkylcarboxyalkyl, $C_6$–$C_{12}$ arylcarboxyalkyl, $C_1$–$C_8$ aminoalkyl, $C_1$–$C_8$ alkylaminoalkyl, $C_1$–$C_8$ dialkylaminoalkyl, $C_1$–$C_8$ trialkylsilylalkyl, wherein each of the aforementioned alkyl moieties may be straight-chain or branched; $C_3$–$C_8$ cycloalkyl, phenyl, ($C_1$–$C_6$ alkyl)phenyl, $C_7$–$C_{12}$ arylalkyl, $C_7$–$C_{12}$ alkarylalkyl, or heterocyclylalkyl, wherein the heterocyclic moiety is morpholinyl, piperidinyl, pyrrolidinyl, piperazinyl, oxiranyl, oxetanyl, furanyl, tetrahydropyranyl or tetrahydrofuranyl; and $R^5$ is i) phenyl or $C_3$–$C_7$ cycloalkyl, optionally substituted by one or more $C_1$–$C_4$ alkyl, preferably one or two methyl; or ii)

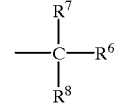

wherein $R^6$ is hydrogen or linear, branched or cyclic, $C_1$–$C_6$ alkyl, $C_1$–$C_6$ hydroxyalkyl, $C_2$–$C_6$ alkenyl, $C_2$–$C_6$ hydroxyalkenyl, $C_2$–$C_6$ alkynyl, $C_2$–$C_6$ hydroxyalkynyl, $C_1$–$C_6$ mono-, di- or tri-haloalkyl or $C_1$–$C_6$ thioalkyl; and $R^7$ and $R^8$ are, independently, hydrogen or, linear, branched or cyclic, $C_1$–$C_6$ alkyl, $C_1$–$C_6$ hydroxyalkyl, $C_2$–$C_6$ alkenyl, $C_2$–$C_6$ hydroxyalkenyl, $C_2-C_6$ alkynyl, $C_2-C_6$ hydroxyalkynyl, $C_1-C_6$ mono-, di- or tri-haloalkyl or $C_1-C_6$ thioalkyl;

b) a second HIV-1 RT inhibitor compound which does not select for the same HIV-1 mutant strain or strains selected for by the first HIV-1 RT inhibitor compound of a); and c) optionally, a third HIV RT inhibitor compound.

This invention also relates to a method for preventing or treating an HIV-1 infection in a patient which comprises administering to the patient, separately or in combination, the first HIV-1 RT inhibitor compound of a) above, a second HIV-1 RT inhibitor which does not select for the same HIV-1 mutant strain or strains selected for by the first HIV-1 RT inhibitor compound of a), and, optionally, a third HIV RT inhibitor compound.

DETAILED DESCRIPTION OF THE INVENTION

The term "HIV-1 RT inhibitor compound" means any compound which inhibits the replication of HIV-1 by interfering with the function of the reverse transcriptase enzyme of HIV-1.

The term "HIV RT inhibitor compound" means any compound which inhibits the replication of any type or strain of HIV, e.g., HIV-1 or HIV-2, by interfering with the function of the reverse transcriptase enzyme of the HIV.

For the purposes of this invention, "select for a HIV-1 mutant strain or strains" means the mutant HIV-1 strain or strains which are resistant to a particular HIV-1 RT inhibitor compound.

To determine which HIV-1 mutant strain or strains, a particular HIV-1 RT inhibitor compound selects for, one can use the method described in Balzarini I and Balzarini II.

Compounds useful in the composition of this invention as the second HIV-1 RT inhibitor compound can be any RT inhibitor compound which does not select for the same HIV-1 mutant strain or strains as the first HIV-1 RT inhibitor compound of formula I. Such HIV-1 RT inhibitor compounds are known and include, for example, the TSAO derivatives described in U.S. application Ser. No. 07/939, 410, filed on Sep. 3, 1992, Camarasa et al, J. Med. Chem. 35(15): 2721–2727 (1992) and Perez—Perez et al, J. Med. Chem. 35(16): 2988–2995 (1992); dipyridodiazepinones such as nevirapine, Merluzzi et al, Science 250: 1411–1413 (1990); pyridinone derivatives, such as 3-{[(4,7-dichloro-1, 3-benzoxazol-2 -yl)methyl]amino}-5-ethyl-6-methylpyridin-2(1H)-one (L-697,661), described in Goldman et al, Proc. Natl. Acad. Sci. USA 88: 6863–6867 (1991); quinoxaline, such as quinoxaline S-2720, as described in Kleim et al, Antimicrob. Agents Chemother. 37, 1659–1664 (1993); bis(heteroaryl)piperazine (BHAP) derivatives, such as N-isopropyl-2-[4-(2-ketoindolyl)-1-piperazinyl]-3-pyridinamine (BHAP U-88204), as described in Romero et al, Proc. Natl. Acad. Sci. USA 88: 8806–8810 (1991); tetrahydroimidazo[4,5,1-jk][(1,4)-benzodiazepin-2(1H)-one and -thione (TIBO) derivatives, such as (+)-S-4,5,6,7-tetrahydro-9-chloro-5-methyl-6-(3-methyl-2-butenyl-imidazo[4,5,1-jk][1,4]-benzodiazepin-2(1H)-thione (R82913), as described in Pauwels et al, Nature 343: 470–474 (1990); coumarin derivatives such as calanolide A, Kashman et al, J. Med. Chem. 35, 2735–2743 (1992); diarylsulfones such as nitrophenylphenylsulfone (NPPS), McMahon et al, Antimicrobial. Agents Chemother. 37, 754–760 (1993); anilidophenylacetamides (alpha-APA) such as R89439, Pauwels et al, Proc. Natl. Acad. Sci. (USA)

90, 1711–1715 (1993); phenethylthiazolethiourea derivatives (PETT) such as LY 300046.HCl, Zhang et al, Abstr. 2nd Int. Workshop on HIV Drug Resistance (Jun. 3–5, Noordwisk, The Netherlands)(1993) no. 30; 1-[(2-hydroxyethoxy)methyl]-6-(phenylthio)thymine (HEPT) derivatives, Baba et al, Biochem. Biophys. Res. Comm. 165, 1375–1381 (1989).

The optional third HIV RT inhibitor compound of c) can be any HIV RT inhibitor compound other than the first HIV-1 RT inhibitor or the second HIV-1 RT inhibitor. Such HIV RT inhibitor compounds are known and include such compounds as, e.g., the HIV-1 RT inhibitor compounds described above as useful as the second HIV-1 RT inhibitor compound or HIV reverse transcriptase inhibitors which do not discriminate between HIV-1 and HIV-2, such as, for example, zidovudine (AZT), didanosine (ddI), zalcitabine (ddC), (−)-2'-deoxy-3'-thiacytidine (3TC), D4T, PMEA, and the like. Preferably, the optional HIV RT inhibitor compound of c) is an HIV RT inhibitor compound which does not select for the same HIV-1 mutant strain or strains as the first HIV-1 RT inhibitor compound or the second HIV-1 RT inhibitor compound, such as a third HIV-1 RT inhibitor compound which does not select for the same HIV-1 mutant strain or strains as the first HIV-1 RT inhibitor compound or the second HIV-1 RT inhibitor compound.

Preferably, this invention relates to a composition for the prevention or treatment of HIV-1 infections which comprises a therapeutically effective amount of:

a) a first HIV-1 RT inhibitor compound of the formula

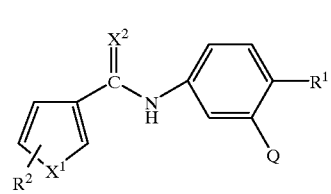

(I)

wherein $X^1$ is O or S, preferably O;

$X^2$ is O or S, preferably S;

Q is

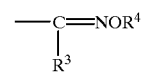

or, preferably, $COYR^5$;

Y is O or S, preferably O;

$R^1$ is hydrogen, halogen, $C_1-C_4$ alkyl, $C_1-C_4$ alkoxy, $C_3-C_4$ alkenyloxy, $C_3-C_4$ alkynyloxy, mono-, di- or trihalomethyl, trifluoromethoxy, $C_1-C_4$ alkylthio, $C_3-C_4$ branched alkylthio, nitro, or cyano, preferably, hydrogen, halogen or $C_1-C_4$ alkyl, and, more preferably, halogen;

$R^2$ is hydrogen, $C_1-C_4$ alkyl or halogen, preferably hydrogen or $C_1-C_4$ alkyl, and, more preferably, hydrogen, methyl or ethyl;

$R^3$ is hydrogen or $C_1-C_4$ alkyl;

$R^4$ is $C_3-C_6$ alkyl, $C_3-C_6$ alkenyl, $C_3-C_6$ alkynyl, $C_1-C_8$ haloalkyl, $C_1-C_8$ alkoxyalkyl, $C_1-C_8$ alkylthioalkyl, $C_1-C_8$ hydroxyalkyl, $C_1-C_8$ acyloxyalkyl, $C_1-C_8$ aroyloxyalkyl, $C_1-C_8$ carboxyalkyl, $C_1-C_8$ alkylcarboxyalkyl, $C_6-C_{12}$ arylcarboxyalkyl, $C_1C_8$ aminoalkyl, $C_1$-$C_8$ alkylaminoalkyl, $C_1$–$C_8$ dialkylaminoalkyl, $C_1$–$C_8$ trialkylsilylalkyl, wherein each of the aforementioned alkyl moieties may be straight-chain or branched; $C_3$–$C_8$ cycloalkyl, phenyl, ($C_1$–$C_6$ alkyl)phenyl, $C_7$–$C_{12}$ arylalkyl, $C_7$–$C_{12}$ alkarylalkyl, or heterocyclylalkyl, wherein the heterocyclic moiety is morpholinyl, piperidinyl, pyrrolidinyl, piperazinyl, oxiranyl, oxetanyl, furanyl, tetrahydropyranyl or tetrahydrofuranyl, preferably, $C_3$–$C_6$ alkyl, $C_3$–$C_6$ alkenyl, $C_3$–$C_6$ alkynyl, $C_1$–$C_8$ haloalkyl, ($C_1$–$C_8$ alkyl)thio($C_1$–$C_8$ alkyl), $C_3$–$C_8$ cycloalkyl or phenyl; and $R^5$ is
i) phenyl or $C_3$–$C_7$ cycloalkyl, optionally substituted by one or more $C_1$–$C_4$ alkyl, preferably one or two methyl; or
ii)

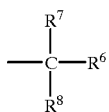

wherein $R^6$ is hydrogen or linear, branched or cyclic, $C_1$–$C_6$ alkyl, $C_1$–$C_6$ hydroxyalkyl, $C_2$–$C_6$ alkenyl, $C_2$–$C_6$ hydroxyalkenyl, $C_2$–$C_6$ alkynyl, $C_2$–$C_6$ hydroxyalkynyl, $C_1$–$C_6$ mono-, di- or tri-haloalkyl or $C_1$–$C_6$ thioalkyl, preferably $C_3$–$C_6$ alkyl, $C_1$–$C_6$ mono-, di- or tri-haloalkyl or $C_1$–$C_6$ thioalkyl; and $R^7$ and $R^8$ are, independently, hydrogen or, linear, branched or cyclic, $C_1$–$C_6$ alkyl, $C_1$–$C_6$ hydroxyalkyl, $C_2$–$C_6$ alkenyl, $C_2$–$C_6$ hydroxyalkenyl, $C_2$–$C_6$ alkynyl, $C_2$–$C_6$ hydroxyalkynyl, $C_1$–$C_6$ mono-, di- or tri-haloalkyl or $C_1$–$C_6$ thioalkyl, preferably, hydrogen or $C_1$–$C_4$ alkyl, and more preferably, hydrogen;

b) a second HIV-1 RT inhibitor compound of the formula

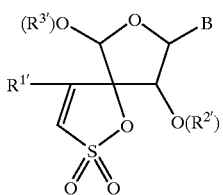

wherein:

B is
i) a pyrimidine of the formula

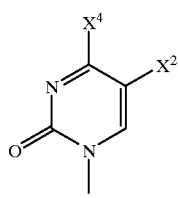 or 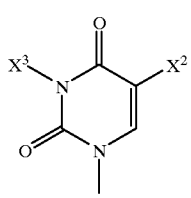

preferably, a pyrimidine of the formula

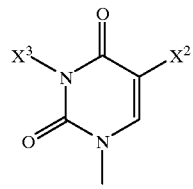

wherein
$X^2$ is a hydrogen, $C_1$–$C_4$ alkyl, $C_2$–$C_4$ alkenyl, $C_2$–$C_4$ alkynyl, halogen, cyano, thiocyano, hydroxymethyl, $C_1$–$C_2$ haloalkyl, nitro or amino, preferably, hydrogen or $C_1$–$C_4$ alkyl;
$X^3$ is hydrogen, $C_1$–$C_4$ alkyl, $C_2$–$C_4$ alkenyl or $C_2$–$C_4$ alkynyl, preferably, hydrogen or $C_1$–$C_4$ alkyl;
$X^4$ is OH, SH, $NH_2$, $NHCH_3$, $N(CH_3)_2$ or $NHCOCH_3$, preferably, $NH_2$, $NHCH_3$ or $N(CH_3)_2$;
ii) a purine of the formula

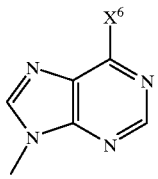 or 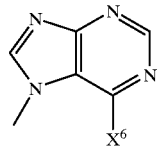

or, preferably, of the formula

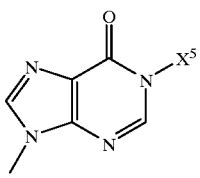 or 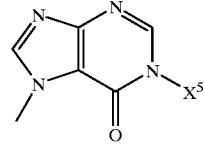

wherein
$X^5$ is H or, preferably, $C_1$–$C_4$ alkyl; and
$X^6$ is H, OH, halogen, $NH_2$, $NHCH_3$ or $N(CH_3)_2$; or
(iii) a triazole of the formula

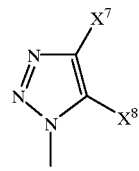

wherein
$X^7$ and $X^8$ are each independently hydrogen, $C_1$–$C_4$ alkyl, $C_1$–$C_4$ haloalkyl, trimethylsilyl, acetyl, $C_1$–$C_6$ alkoxycarbonyl, $C_1$–$C_6$ alkylcarbonyl, $CONH_2$, $CONHCH_3$, $CON(CH_3)_2$, or, preferably, $NH_2$, $NHCH_3$ or $N(CH_3)_2$;
$R^{1'}$ is amino, $C_1$–$C_4$ aminoalkyl, $C_2$–$C_4$ aminoalkenyl or $C_2$–$C_4$ aminoalkynyl, preferably, amino or $C_1$–$C_4$ aminoalkyl; and
$R^{2'}$ and $R^{3'}$ are each independently, silyl tri-substituted by the same or different, phenyl or $C_1$–$C_4$ linear or branched alkyl; and c) optionally, a third HIV RT inhibitor compound which does not select for the same HIV-1 mutant strain or strains selected for by either the first HIV-1 RT inhibitor compound of a) or the second HIV-1 RT inhibitor compound of b).

More preferably, this invention relates to a composition for the prevention or treatment of HIV-1 infections which comprises a therapeutically effective amount of:

a) a first HIV-1 RT inhibitor compound of the formula

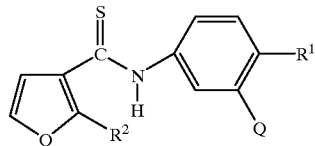

wherein

Q is 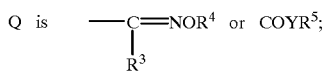

Y is O;

$R^1$ is hydrogen, halogen, or $C_1$–$C_4$ alkyl;

$R^2$ is hydrogen or $C_1$–$C_4$ alkyl;

$R^3$ is hydrogen or $C_1$–$C_4$ alkyl;

$R^4$ is $C_3$–$C_6$ alkyl, $C_3$–$C_6$ alkenyl, $C_3$–$C_6$ alkynyl, $C_1$–$C_8$ haloalkyl, or ($C_1$–$C_8$ alkyl)thio($C_1$–$C_8$)alkyl, wherein each of the aforementioned alkyl moieties may be straight-chain or branched; $C_3$–$C_8$ cycloalkyl or phenyl; and $R^5$ is i) phenyl or $C_3$–$C_7$ cycloalkyl, optionally substituted by one or two methyl; or ii)

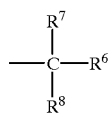

wherein $R^6$ is hydrogen or linear, branched or cyclic, $C_1$–$C_6$ alkyl, $C_1$–$C_6$ hydroxyalkyl, $C_2$–$C_6$ alkenyl, $C_2$–$C_6$ hydroxyalkenyl, $C_2$–$C_6$ alkynyl, $C_2$–$C_6$ hydroxyalkynyl, $C_1$–$C_6$ mono-, di- or tri-haloalkyl or $C_1$–$C_6$ thioalkyl; and $R^7$ and $R^8$ are hydrogen or $C_1$–$C_4$ alkyl, linear, branched or cyclic;

b) a second HIV-1 RT inhibitor compound of the formula

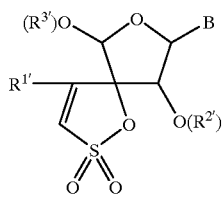

wherein:

B is i) a pyrimidine of the formula

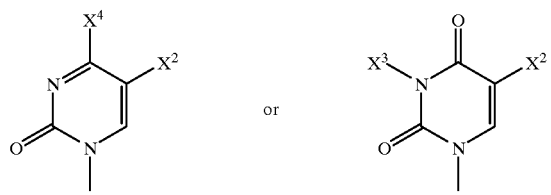

wherein $X^2$ is a hydrogen or $C_1$–$C_4$ alkyl;

$X^3$ is hydrogen or $C_1$–$C_4$ alkyl;

$X^4$ is $NH_2$, $NHCH_3$ or $N(CH_3)_2$;

ii) a purine of the formula

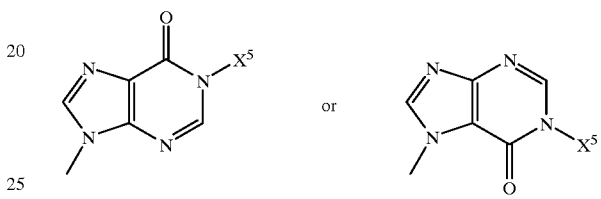

wherein $X^5$ is $C_1$–$C_4$ alkyl; or (iii) a triazole of the formula

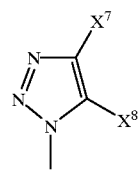

wherein $X^7$ and $X^8$ are each independently hydrogen, $C_1$–$C_4$ alkyl, $C_1$–$C_4$ haloalkyl, trimethylsilyl, acetyl, $C_1$–$C_6$ alkoxycarbonyl, $C_1$–$C_6$ alkylcarbonyl, $CONH_2$, $CONHCH_3$, $CON(CH_3)_2$, or, preferably, $NH_2$, $NHCH_3$ or $N(CH_3)_2$;

$R^1$ is amino or $C_1$–$C_4$ aminoalkyl; and $R^{2'}$ and $R^{3'}$ are each independently, silyl tri-substituted by the same or different, phenyl or $C_1$–$C_4$ linear or branched alkyl; and c) optionally, a third HIV RT inhibitor compound which does not select for the same HIV-1 mutant strain or strains selected for by either the first HIV-1 RT inhibitor compound of a) or the second HIV-1 RT inhibitor compound of b).

Most preferably, this invention relates to a composition for the prevention or treatment of HIV-1 infections which comprises a therapeutically effective amount of:

a) a first HIV-1 RT inhibitor compound of the formula

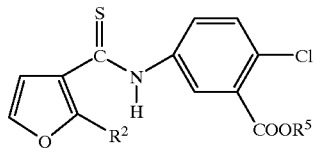

wherein $R^2$ is hydrogen, methyl or ethyl; and
$R^5$ is
i) phenyl or $C_3$–$C_7$ cycloalkyl; or
ii)

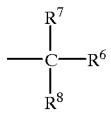

wherein
$R^6$ is hydrogen or linear, branched or cyclic, $C_3$–$C_6$ alkyl, $C_1$–$C_6$ mono-, di- or tri-haloalkyl or $C_1$–$C_6$ thioalkyl; and
$R^7$ and $R^8$ are hydrogen;
b) a second HIV-1 RT inhibitor compound of the formula

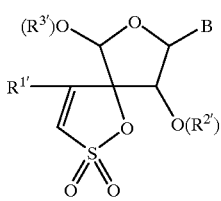

wherein:
B is
i) a pyrimidine of the formula

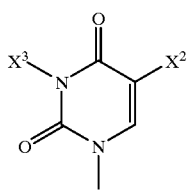

wherein
$X^2$ is a hydrogen or $C_1$–$C_4$ alkyl;
$X^3$ is hydrogen or $C_1$–$C_4$ alkyl;
ii) a purine of the formula

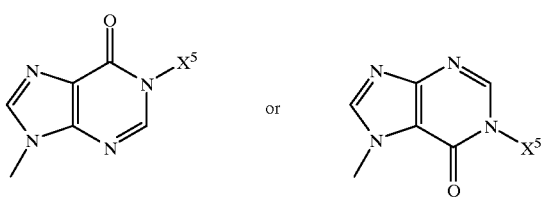

or wherein $X^5$ is $C_1$–$C_4$ alkyl; or
(iii) a triazole of the formula

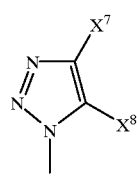

wherein $X^7$ and $X^8$ are each independently $NH_2$, $NHCH_3$ or $N(CH_3)_2$;
$R^{1'}$ is amino or $C_1$–$C_4$ aminoalkyl; and
$R^{2'}$ and $R^{3'}$ are each independently, silyl tri-substituted by the same or different, phenyl or $C_1$–$C_4$ linear or branched alkyl; and
c) optionally, a third HIV RT inhibitor compound which does not select for the same HIV-1 mutant strain or strains selected for by either the first HIV-1 RT inhibitor compound of a) or the second HIV-1 RT inhibitor compound of b).

Compounds of formula I useful as the first HIV-1 RT inhibitor compounds in the composition of this invention can be prepared, e.g., as described in U.S. Pat. No. 5,268,389. TSAO compounds useful as the second HIV-1 RT inhibitor compounds in the composition of this invention can be prepared, e.g., as described in published European Patent Application No. 0 530 407.

The composition of the present invention can be administered orally, parenterally, sublingually, by inhalation spray, rectally, or topically in dosage unit formulations containing conventional non-toxic pharmaceutically acceptable carriers, adjuvants, and vehicles. Suitable carriers, adjuvants and vehicles can be found in standard pharmaceutical texts such as, e.g., *Remington's Pharmaceutical Sciences,* 16th Edition, Mack Publishing Company, Easton, Pa. (1980).

The therapeutically effective amount of the active ingredients that can be combined with the carrier to produce a single dosage form will vary depending upon the age and condition of the host treated and the particular mode of administration. In general, the active ingredients of the composition of this invention are most desirably administered at a concentration level that will generally afford anti-virally effective results without causing any harmful or deleterious side effects.

The ratio of the first HIV-1 RT inhibitor compound to the second HIV-1 RT inhibitor compound in the composition of this invention can vary depending on the first HIV-1 RT inhibitor compound and the second HIV-1 RT inhibitor compound selected and on the symptoms and/or severity of the HIV-1 infection, but will usually be from about 1:100 to about 100:1 by weight, preferably from about 1:5 to about 5:1 by weight. In the composition of this invention comprising the optional third HIV RT inhibitor compound, the percent amount of third HIV RT inhibitor compound in the composition will vary depending on the symptoms and/or severity of the HIV-1 infection and on the third HIV RT inhibitor compound selected, but will usually be from about 1% to about 99% by weight of the total composition, preferably from about 20% to about 80% by weight of the total composition.

The first HIV-1 RT inhibitor compound, the second HIV-1 RT inhibitor compound, and the third HIV RT inhibitor compound, if selected, can be administered to a patient as a composition comprising all the ingredients, or the ingredients can be administered separately to the patient. For example, the first HIV-1 RT inhibitor compound can be administered to the patient first, then the second HIV-1 RT inhibitor compound can be administered to the patient, and then, if selected, the third HIV RT inhibitor compound can be administered. Alternatively, for example, the second HIV-1 RT inhibitor compound can be administered to the patient first, then the first HIV-1 RT inhibitor compound, and then, if selected, the third HIV RT inhibitor compound. Or, for example, if selected, the third HIV RT inhibitor compound can be administered first to the patient and then followed by the administration of the first HIV-1 RT inhibitor compound and the second HIV-1 RT inhibitor. Or, the first and second HIV-1 RT inhibitor compound can be administered to the patient as a composition, then the third HIV RT inhibitor can be administered. Or, the first HIV-1 RT inhibitor compound and third HIV RT inhibitor compound can be administered to the patient as a composition, then the second HIV-1 RT inhibitor compound can be administered. Or, the second HIV-1 RT inhibitor compound and the third HIV RT inhibitor compound can be administered to the patient first, then the first HIV-1 RT inhibitor compound can be administered, and so forth.

While the active ingredients of the composition of this invention can be administered as the sole active pharmaceutical agents, the active ingredients can also be used in combination with one or more other pharmaceutical agents which are not deleterious to the activity of the active ingredients of the composition of this invention or whose combination with the active ingredients will not have a deleterious effect on the host treated.

The following examples are provided to illustrate the present invention.

EXAMPLES

Materials and Methods

Test compounds

The TSAO derivative [1-[2',5'-bis-O-(tert-butyldimethylsilyl)-β-D-ribofuranosyl]-3-N-methylthymine-3'-spiro-5"-(4"-amino-1",2"-oxathiole 2",2"-dioxide (TSAO-m³T) was synthesized as described in Perez-Perez et al, supra. TIBO R82913 was provided by Zhang Hao (National Institutes of Health, Bethesda, Md.) or obtained from Pharmatech International Inc. (West Orange, N.J.). Nevirapine (BI-RG-587) and pyridinone L-697,661 were provided by Boehringer Ingelheim Pharmaceuticals, Inc. (Ridgefield, Conn.) and Merck, Sharp & Dohme (West Point, Pa.), respectively. BHAP U-88204 (N-isopropyl-2-[4-(2-ketoindolyl)-1-piperazinyl]-3-pyridinamine) was obtained from The Upjohn Company (Kalamazoo, Mich.) and BHAP U-90152 was obtained from Hoechst AG (Frankfurt, Germany). MCK-442 was provided by Fukushima Medical College (Fukushima, Japan). Compounds I, II, III, IV, and V, tabulated in Table A below, were prepared using the procedures described in U.S. Pat. No. 5,268,389.

TABLE A

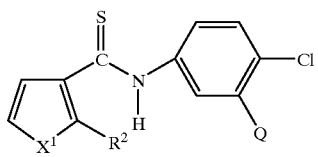

| COMPOUND | X¹ | R² | Q |
|---|---|---|---|
| I | O | CH₃ | CHNOC(CH₃)₃ |
| II | O | CH₃ | COOCH₂CH(CH₃)₂ |
| III | O | CH₃ | COO-cyclohexyl |
| IV | O | CH₃ | COO-cyclopentyl |
| V | S | H | COO-cyclohexyl |

BHAP U-90152 has the following structure:

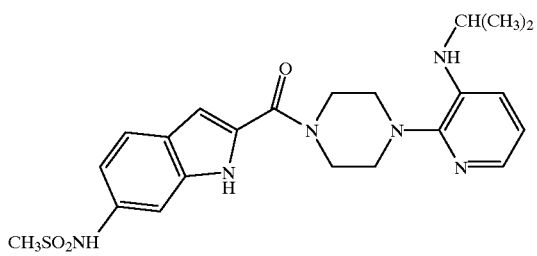

MCK-442 has the following structure:

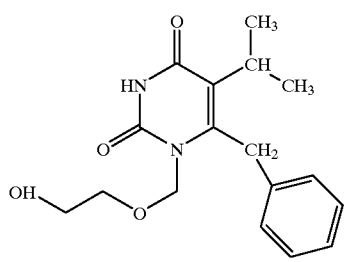

Cells and viruses
CEM cells were obtained from the American Tissue Cell Culture Collection (Rockville, Md.). HIV-l(IIIB) was originally obtained from the culture supernatant of persistently HIV-1-infected H9 cells and was provided by R. C. Gallo and M. Popovic (National Institutes of Health, Bethesda, Md.).
Selection of HIV-1(III$_B$) mutant strains resistant to HIV-1-specific RT inhibitors administered as a single drug or in combination
HIV-l(III,) was subjected to two to three passages in 5 ml CEM cell cultures (4×10⁵ cells per ml) in the presence of several fixed concentrations of the test compounds in 25 cm² culture flasks (Falcon; Becton Dickinson) to produce mutant HIV-1 strains. The culture medium consisted of RPMI 1640 containing 10% fetal bovine serum, 2 mM L-glutamine, and 0.075% NaHCO₃. The multiplicity of the initial infection was ~1000 times the CCID₅₀(50% cell culture infective dose). Passages were performed every 3 to 4 days by adding 0.5 to 1.0 ml of the infected culture supernatant to 5 ml of a suspension containing 4×10⁵ uninfected CEM cells per ml. Syncytium formation was used as a parameter of virus breakthrough in the cell cultures. In the drug combination experiments, the compounds were combined at the same initial concentrations as used for the two lowest concentrations in the single-drug experiments.
Sensitivity of several HIV-1 mutant strains to the test compounds in CEM cell cultures
CEM cells were suspended at 250,000 cells per ml of culture medium and infected with wild-type HIV-I(III$_B$) or mutant HIV-1 strains at 100 50% cell culture infective doses per ml. Then 100 μl of the infected cell suspensions was added to 200-μl microtiter plate wells containing 100 μl of an appropriate dilution of the test compounds. After 4 days incubation at 37° C., the cell cultures were examined for syncytium formation. The 50% effective concentration (EC₅₀) was determined as the compound concentration required to inhibit HIV-1-induced syncytium formation by 50%.
Preparation of mutant HIV-1-infected CEM cell cultures for polymerase chain reaction analysis and sequencing of the pol gene of the mutant HIV-1 strains The procedure that was utilized is described in Balzarini I, supra, and Balzarini et al, Proc. Natl. Acad. Sci. USA 90: 6952–6956 (1993)("Balzarini III"). Oligonucleotides were chosen to give a 727-bp fragment covering RT amino acids 50 to 270. Amplification of proviral DNA (35 cycles) was performed with extract from $1 \times 10^5$ cells in 10 mM Tris.HCl (pH 8.8), 50 mM KCl, 1.5 mM $MgCl_2$, 0.1% Triton X-100, 2.5 units of thermostable DNA polymerase (Dyna Zyme, Finnzymes Inc.) and 15 µM of each primer in a final volume of 100 µl. The first set of primers (5'-GTAGAATTCTGTTGACTCAGATTGG and 5'-TTCTGCCAGTTCTAGCTCTGCTTCT) gave a 900-bp product of the proviral reverse transcriptase gene. One tenth of the reaction from the first PCR was then transferred as template to a new 35-cycle PCR with a second set of primers (5'-CCTGAAAATCCATACAATACTCCAGTATTTG and 5'-AGTGCTTTGGTTCCTCTAAGGAGTTTAC) which gave a 727-bp reverse transcriptase fragment covering the amino acids 50–270. The second set of oligonucleotides primed for DNA synthesis internally from the first set of oligonucleotides and thereby amplified specific products from the first PCR, while unspecific products were not further amplified. The PCR products were made visible on a 1% agarose gel.

Reverse transcriptase assay

The reaction mixture (50 µl) contained 50 mM Tris.HCl, pH 7.8, 5 mM dithiothreitol, 300 mM glutathione, 500 µM EDTA, 150 mM KCl, 5 mM $MgCl_2$, 1.25 µg of bovine serum albumin, a fixed concentration of the labeled substrate $[2,8-^3H]dGTP$ (2.95 µM, 2 µCi), a fixed concentration of the template/primer poly(C).oligo(dG) (0.1 mM), 0.06% Triton X-100, 5 µl of inhibitor solution [containing various concentrations (5-fold dilutions) of the test compounds], and 5 µl of the RT preparation. The reaction mixtures were incubated at 37° C. for 30 min, at which time 100 µl of calf thymus DNA (150 µg/ml), 2 ml of $Na_4P_2O_7$ (0.1 M in 1M HCl), and 2 ml of trichloroacetic acid (10%, v/v) were added. The solutions were kept on ice for 30 min, after which the acid-insoluble material was washed and analyzed for radioactivity. The $IC_{50}$ of the test compounds was determined as the compound concentration that inhibited the virus particle-derived RT activity by 50%.

Results

Antiviral activity spectrum of Compounds I, II, III, IV, and V

Compounds, I, II, III, IV and V, proved markedly inhibitory to HIV-1($III_B$) replication in CEM cells. Their 50% inhibitory concentration ranged between 0.004 and 0.05 µg/ml. The inhibitory activity of the most active of Compounds I, II, III, IV and V against wild-type HIV-1 was superior to that of the HIV-1-specific RT inhibitors nevirapine, BHAP, pyridinone, TIBO and TSAO-$m^3T$ (Table 1). However, in striking contrast with the latter HIV-1-specific RT inhibitors, Compounds I, II, III, IV, and V, proved substantially more inhibitory to the cytopathicity of the pyridinone-resistant RT/181-Cys HIV-1 mutant in CEM cells. As a rule, the activity of Compounds I, II, III, IV and V against the RT/181-Cys mutant virus was at least one to two orders of magnitude more pronounced than that of the other HIV-1-specific RT inhibitors.

Also, the antiviral potency of Compounds I, II, III, IV and V against other mutant HIV-1 strains containing the 138 Glu→Lys and 106 Val→Ala mutations in their RT was at least 10- to 50-fold more pronounced than noted for the other compounds. Compounds I, II, III, IV and V were less active against the RT/100-Ile mutant and the RT/103-Asn mutant virus strains than against wild-type virus. Yet, their antiviral potency was still in the ng/ml range, which is lower than for other HIV-1 specific RT inhibitors, which had $EC_{50}$ values close to or even markedly higher than 1 µg/ml (Table 1).

TABLE 1

SENSITIVITY/RESISTANCE SPECTRUM OF DIFFERENT MUTANT HIV-1 STRAINS

| | 50% Effective Concentration (µg/ml) | | | | | |
|---|---|---|---|---|---|---|
| Compound | HIV-1 ($III_B$) (WT*) | HIV-1/ TIBO R82150[b] (100-Ile) | HIV-1/ TIBO R82913[b] (103-Asn) | HIV-1/ Nev[b] (106-Ala) | HIV-1/ TSAO-$m^3T$[b] (138-Lys) | HIV-1/ Pyr[b] (181-Cys) |
| I | 0.050 ± 0.014 | 0.085 ± 0.007 | ≧1 | 0.130 ± 0.040 | 0.075 ± 0.007 | 0.075 ± 0.007 |
| II | 0.01 | 0.190 ± 0.16 | 0.45 | 0.075 ± 0.040 | 0.060 ± 0.0 | 0.070 ± 0.03 |
| III | 0.004 ± 0.001 | 0.170 ± 0.12 | 0.70 | 0.057 ± 0.045 | 0.035 ± 0.021 | 0.070 ± 0.03 |
| IV | 0.005 ± 0.0 | 0.170 ± 0.12 | 0.70 | 0.040 ± 0.028 | 0.035 ± 0.007 | 0.045 ± 0.021 |
| V | 0.030 ± 0.020 | 0.850 ± 0.21 | >1 | 0.073 ± 0.025 | 0.075 ± 0.007 | 0.077 ± 0.021 |
| TSAO-$m^3T$ | 0.03 | 0.05 | 0.15 | >50 | >50 | 3.0 |
| Nevirapine | 0.007 ± 0.0 | 0.100 ± 0.06 | 1.5 | 2.3 ± 0.58 | 0.030 ± 0.02 | 2.30 ± 0.58 |
| BHAP U88204 | 0.04 ± 0.007 | 0.75 ± 0.35 | 1.7 | 0.4 ± 0.0 | 0.07 ± 0.02 | 0.40 ± 0.14 |
| Pyridinone L-697,661 | 0.007 ± 0.003 | 0.18 ± 0.08 | 0.5 | 0.24 ± 0.23 | 0.17 ± 0.06 | 3.67 ± 1.15 |
| TIBO R82913 | 0.016 ± 0.008 | 1.75 ± 0.50 | 4.3 | 0.50 ± 0.30 | 0.30 ± 0.0 | 2.0 ± 0.0 |

*WT = wild type
[a]50% Effective concentration, or compound concentration required to inhibit virus-induced cytopathicity in CEM cells by 50%.
[b]Mutant virus strains that contain the 100 Leu → Ile, 103 Lys → Asn, 106 Val → Ala, 138 Glu → Lys or 181 Tyr → Cys mutation in their RT were obtained after selection in cell culture in the presence of TIBO R82150, TIBO R82913, nevirapine, TSAO-$m^3T$ and pyridinone L-697,661, respectively. The amino acid mutations have been characterized in Balzarini I, Balzarini II and Balzarini III, supra.

Inhibitory effect of Compounds I, II, IV and V against HIV-1 RT

Compounds I, III, IV and V were evaluated for their inhibitory effect on recombinant HIV-1 RT. They proved to be very potent inhibitors of the HIV-1 RT, using poly(C) .oligo(dG) as the template primer and 2.95 µM $[2,8-^3H]$ dGTP as the radiolabeled substrate. Their $IC_{50}$ values invariably ranged between 0.018 and 0.077 µg/ml. Higher $IC_{50}$ values were noted for nevirapine, pyridinone, BHAP and TIBO, and the $IC_{50}$ of TSAO-$m^3T$ for HIV-1 RT was even 20- to 50-fold higher than those of Compounds I, II, IV and V (Table 2).

TABLE 2

ANTI-HIV-1 RT (WT) ACTIVITY

| COMPOUND | $IC_{50}$(µg/ml)[a] |
|---|---|
| I | 0.071 ± 0.033 |
| III | 0.055 ± 0.005 |
| IV | 0.018 ± 0.011 |
| V | 0.077 ± 0.002 |
| TSAO-$m^3T$ | 2.78 ± 0.18 |
| Nevirapine | 0.52 ± 0.10 |
| BHAP U88204 | 0.44 ± 0.01 |
| Pyridinone L-697,661 | 0.38 ± 0.05 |
| TIBO R82913 | 0.66 ± 0.17 |

TABLE 2-continued

ANTI-HIV-1 RT (WT) ACTIVITY

| COMPOUND | $IC_{50}(\mu g/ml)^a$ |
|---|---|

[a]50% Inhibitory concentration. Substrate: [2,8-$^3$H]dGTP (2.95 $\mu$M). Template: poly(rC)oligo(dG).

Knock-out concentrations

Compounds I, II, III, IV and V and also BHAP U88204 and nevirapine were added to HIV-I(III$_B$)-infected CEM cells at initial concentrations of 0.1, 0.5 and 2.5 $\mu$g/ml. The drug concentrations were kept constant throughout the whole time period of the experiment (10 subcultivations or 35 days). Then the drugs were removed from the cell cultures, and the cells were further subcultured for at least 5 additional passages. Virus only emerged in the presence of the lowest concentrations (i.e., 0.1 $\mu$g/ml) of Compounds I, II, III and IV. Compound V allowed late virus breakthrough at 0.5 $\mu$g/ml (Table 3). In contrast, virus resistant to the inhibitory effects of 0.1 and 0.5 $\mu$g/ml BHAP and 0.1, 0.5 and 2.5 $\mu$g/ml nevirapine emerged in the infected cell cultures under similar experimental conditions. Thus, Compounds I, II, III, IV and V could prevent virus breakthrough in HIV-1-infected cell cultures at least 5- to 25-fold more efficiently than BHAP or nevirapine, respectively (Table 3). At the 10th subcultivation, the HIV-1-infected CEM cell cultures that were fully protected against HIV-1-induced cytopathicity by the UR derivatives did not produce detectable p24 levels, and lacked any proviral DNA. Also, after removal of the test compounds, and further subcultivation of the cells in the absence of the test compounds, virus did not emerge. Therefore, we may conclude that the HIV-1-infected cell cultures were cleared from virus when cultivated in the presence of markedly lower concentrations of Compounds I, II, III, IV and V than of the other HIV-1-specific RT inhibitors.

Characterization of the mutant HIV-1 strains that emerged under therapy with Compounds I, II, III, IV and V The RT genes of seven mutant HIV-1 strains that emerged under therapy with Compounds I, II, III, IV and V, and with Compounds A and B (defined below), were characterized with regard to potential mutations in their RT. Mutations were found at amino acid positions 100, 101, 103 and 138. Interestingly, three new mutations were discovered. The mutant HIV-1/IV strain contained the 103 Lys→Thr mutation, due to a transversion of the second base (A→C) of codon 103. Compound B selected for a novel mutation at amino acid position 101 of the RT, i.e. substitution of Lys (AAA) by Glu (GAA). When used at 0.1 $\mu$g/ml, Compound V selected for virus containing a double mutation in its RT, namely 101-Lys→Ile and 141-Gly→Glu (Table 4).

The structure of Compound A is

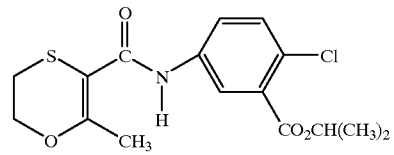

The structure of Compound B is

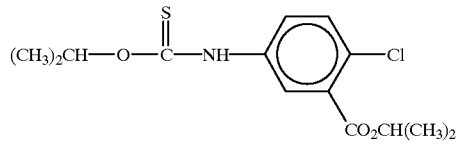

TABLE 4

TABLE 3

BREAKTHROUGH OF HIV-1(III$_B$)-INDUCED CYTOPATHICITY IN CEM CELL CULTURES

ESTIMATION of HIV-1-INDUCED CYTOPATHICITY IN CEL CULTURE (PERCENTAGE OF CONTROL)

| CMPD | CONC. ($\mu$g/ml) | 4 | 8 | 11 | 14 | 17 | 21 | 25 | 28 | 32 | 35$^a$ | 39 | 42 | 46 | 49 | 53 |
|---|---|---|---|---|---|---|---|---|---|---|---|---|---|---|---|---|
| I | 0.1 | 0 | 0 | 6.2 | 25 | 100 | 100 | 100 | 100 | 100 | 100 | 100 | 100 | 100 | 100 | 100 |
|  | 0.5 | 0 | 0 | 0 | 0 | 0 | 0 | 0 | 0 | 0 | 0 | 0 | 0 | 0 | 0 | 0 |
|  | 2.5 | 0 | 0 | 0 | 0 | 0 | 0 | 0 | 0 | 0 | 0 | 0 | 0 | 0 | 0 | 0 |
| II | 0.1 | 0 | 0 | 0 | 12.5 | 50 | 100 | 100 | 100 | 100 | 100 | 100 | 100 | 100 | 100 | 100 |
|  | 0.5 | 0 | 0 | 0 | 0 | 0 | 0 | 0 | 0 | 0 | 0 | 0 | 0 | 0 | 0 | 0 |
|  | 2.5 | 0 | 0 | 0 | 0 | 0 | 0 | 0 | 0 | 0 | 0 | 0 | 0 | 0 | 0 | 0 |
| III | 0.1 | 0 | 0 | 0 | 6.2 | 50 | 100 | 100 | 100 | 100 | 100 | 100 | 100 | 100 | 100 | 100 |
|  | 0.5 | 0 | 0 | 0 | 0 | 0 | 0 | 0 | 0 | 0 | 0 | 0 | 0 | 0 | 0 | 0 |
|  | 2.5 | 0 | 0 | 0 | 0 | 0 | 0 | 0 | 0 | 0 | 0 | 0 | 0 | 0 | 0 | 0 |
| IV | 0.1 | 0 | 0 | 0 | 6.2 | 25 | 87.5 | 100 | 100 | 100 | 100 | 100 | 100 | 100 | 100 | 100 |
|  | 0.5 | 0 | 0 | 0 | 0 | 0 | 0 | 0 | 0 | 0 | 0 | 0 | 0 | 0 | 0 | 0 |
|  | 2.5 | 0 | 0 | 0 | 0 | 0 | 0 | 0 | 0 | 0 | 0 | 0 | 0 | 0 | 0 | 0 |
| V | 0.1 | 0 | 37.5 | 50 | 100 | 100 | 100 | 100 | 100 | 100 | 100 | 100 | 100 | 100 | 100 | 100 |
|  | 0.5 | 0 | 0 | 0 | 18.5 | 75 | 100 | 100 | 100 | 100 | 100 | 100 | 100 | 100 | 100 | 100 |
|  | 2.5 | 0 | 0 | 0 | 0 | 0 | 0 | 0 | 0 | 0 | 0 | 0 | 0 | 0 | 0 | 0 |
| BHAP U88204 | 0.1 | 0 | 12.5 | 50 | 100 | 100 | 100 | 100 | 100 | 100 | 100 | 100 | 100 | 100 | 100 | 100 |
|  | 0.5 | 0 | 0 | 6.25 | 6.25 | 25 | 75 | 87.5 | 100 | 100 | 100 | 100 | 100 | 100 | 100 | 100 |
|  | 2.5 | 0 | 0 | 0 | 0 | 0 | 0 | 0 | 0 | 0 | 0 | 0 | 0 | 0 | 0 | 0 |
| Nevirapine | 0.1 | 37.5 | 87.5 | 100 | 100 | 100 | 100 | 100 | 100 | 100 | 100 | 100 | 100 | 100 | 100 | 100 |
|  | 0.5 | 6.25 | 25 | 50 | 100 | 100 | 100 | 100 | 100 | 100 | 100 | 100 | 100 | 100 | 100 | 100 |
|  | 2.5 | 0 | 0 | 6.25 | 25 | 62.5 | 100 | 100 | 100 | 100 | 100 | 100 | 100 | 100 | 100 | 100 |

[a]From the 35th day onwards, all subcultivations took place in the absence of the test compounds.

| COMPOUND | AMINO ACID POSITION | AMINO ACID | CODON |
|---|---|---|---|
| AMINO ACID MUTATIONS IN THE REVERSE TRANSCRIPTASE OF MUTANT HIV-1 STRAINS, OBTAINED UNDER SELECTIVE PRESSURE OF COMPOUNDS A, B, I, II, III, IV, V, BHAP OR NEVIRAPINE | | | |
| A | 138 | Glu→Lys | GAG→AAG |
| B | 101 | Lys→Glu | AAA→GAA |
| I/0.1 | 103 | Lys→Asn | AAA→AAC |
| II/0.1 | 100 | Leu→Ile | TTA→ATA |
| III/0.1 | 103 | Lys→Asn | AAA→AAC |
| IV/0.1 | 103 | Lys→Thr | AAA→ACA |
| V/0.1 | 101 | Lys→Ile | AAA→ATA |
|  | +141 | Gly→Glu | GGG→GAG |
| V/0.5 | 103 | Lys→Asn | AAA→AAC |
| BHAP U88204/0.1 | 181 | Tyr→Cys | TAT→TGT |
| BHAP U88204/0.5 | 181 | Tyr→Cys | TAT→TGT |
| Nevirapine | 106 | Val→Ala | GTA→GCA |

The other mutant viruses that emerged under therapy with Compounds I, II, III, IV, V, A and B, contained amino acid changes at positions 100, 101, 103 and 138 in their RT that have been reported previously for other HIV-1-specific RT inhibitors, including TIBO R82150, TIBO R82913, BHAP U88204, pyridinone L-697,661 and TSAO derivatives. The virus that emerged under BHAP and nevirapine treatment contained in their RT the 181 Tyr→Cys and 106 Val→Ala mutation, respectively.

Sensitivity/resistance of mutant HIV-1 strains towards other HIV-1-specific RT inhibitors The mutant HIV-1/B containing the novel 101 Lys→Glu mutation in its RT showed a peculiar resistance pattern. Compound I, as well as all other HIV-1 specific inhibitors, became less effective against this virus strain by at least 2 to 3 orders of magnitude (EC$_{50}$: ≧1 μg/ml). However, pyridinone L-697,661 retained a marked inhibitory efficacy against this mutant virus strain (EC$_{50}$: 0.035 μg/ml) (Table 5). The three mutant HIV-1 strains containing the 103 Lys→Asn mutation in their RT markedly differed in their sensitivity spectrum to the HIV-1-specific inhibitors. For example, TIBO, BHAP, nevirapine, pyridinone and MKC-442 were 10- to 30-fold more inhibitory to HIV-1/III(0.1) than HIV-I/V(0.5). Compounds I, II and IV were only 3- to 5-fold less inhibitory to HIV-1/V(0.5) than HIV-1/III(0.1), whereas TSAO-m$^3$T was equally inhibitory to both virus mutants. The third RT/103-Asn mutant virus strain [HIV-I/I(0.1)] showed a resistance/sensitivity spectrum to the HIV-1-specific RT inhibitors that was intermediate between that of both other RT/103-Asn mutant viruses. The HIV-1/V(0.1) strain containing the double (101 Lys→Ile+141 Gly→Glu) mutation retained marked sensitivity to several compounds, including pyridinone, TSAO-m$^3$T, MKC-442, and even Compounds II and III.

TABLE 5

SENSITIVITY/RESISTANCE SPECTRUM OF HIV-1 MUTANTS TO HIV-1-SPECIFIC RT INHIBITORS EC50$^a$ (μg/ml)

| COMPOUND | HIV-1 (III$_B$) | HIV-1/ I(0.1) 103-Asn | HIV-1/ II(0.1) 100-Ile | HIV-1/ III(0.1) 103-Asn | HIV-1/ IV(0.1) 103-Thr | HIV-1/ V(0.1) 101-Ile + 141-Glu | HIV-1/ V(0.5) 103-Asn | HIV-1/ B 101Glu |
|---|---|---|---|---|---|---|---|---|
| I | 0.010 | 0.23 | 1.25 | 0.30 | 0.60 | 0.12 | 0.73 | 1.5 |
| II | 0.007 | 0.15 | 0.5 | 0.16 | 0.40 | 0.06 | 0.80 | — |
| III | 0.004 | 0.30 | 0.87 | 0.16 | 1.1 | 0.05 | 0.85 | — |
| IV | 0.005 | 0.20 | 0.4 | 0.14 | 0.53 | 0.11 | 0.65 | — |
| V | 0.03 | 1.75 | ≧5 | 0.35 | 2.75 | 0.30 | ≧5 | — |
| TIBO R82913 | 0.020 | 1.1 | ≧5 | 0.23 | ≧5 | 0.16 | 5.0 | >2.5 |
| BHAP U90152 | 0.010$^b$ | 0.25 | 0.67 | 0.05 | 0.47 | 0.10 | 0.50 | 1.0$^b$ |
| Nevirapine | 0.007 | 1.7 | ≧5 | 0.38 | 2.7 | 0.24 | ≧5 | >2.5 |
| Pyridinone L-697,661 | 0.007 | 0.30 | 0.63 | 0.03 | 0.50 | 0.08 | 0.55 | 0.035 |
| TSAO-m$^3$T | 0.030 | 0.22 | 0.37 | 0.20 | 0.30 | 0.06 | 0.30 | >2.5 |
| MKC-442 | 0.0006 | 0.08 | 0.40 | 0.01 | 0.32 | 0.008 | 0.35 | — |
| 3TC* | 0.008 | 0.03 | 0.05 | 0.03 | 0.03 | 0.04 | 0.04 | — |

*(-)-2'-deoxy-3'-thiacytidine

Finally, the HIV-1/IV(0.1) mutant strain, containing the novel Thr mutation at position 103 of its RT, retained sensitivity to most HIV-1-specific inhibitors in the ng/ml range, except for nevirapine, TIBO R82913, Compound III and Compound V, which inhibited this mutant virus only at an EC$_{50}$ of 1.1 to 2.75 μg/ml.

Double- and triple-drug combination treatment with Compound IV, TSAO-m3T and/or BHAP U90152

Compound IV, BHAP and TSAO-m$^3$T were added to HIV-1-infected CEM cell cultures at 0.04, 0.10 and 0.25 ug/ml (Compound IV and BHAP) or 1.0, 2.5 and 5.0 μg/ml (TSAO-m$^3$T). In addition, various double- and triple-drug combinations of Compound IV, BHAP and TSAO-m$^3$T were performed, combining these inhibitors at their lowest (0.04 μg/ml) or intermediary (0.1 μg/ml) concentration as used in the single-drug experiments. Under our experimental conditions, mutant virus emerged under single-drug therapy at all concentrations evaluated. Under certain conditions, virus emerged as fast as 7 to 11 days after initiation of the experiment. At best, virus breakthrough could be delayed till day 14 (at the higher concentrations of BHAP and TSAO) or day 21 (at the highest concentration of Compound IV) (Table 6).

However, when Compound IV and TSAO-m$^3$T were combined at their lowest concentrations (i.e. 0.04 μg/ml for Compound IV and 1.0 μg/ml for TSAO-m$^3$T), the first signs of HIV-1-induced cytopathicity appeared at day 18 post infection, whereas the combination of Compound IV at 0.04 μg/ml with TSAO-m$^3$T at 2.5 μg/ml delayed virus breakthrough for 28 days post infection, that is for a much longer time than when both compounds were added to the cell cultures as single drugs at the same or at 2.5-fold (TSAO-m$^3$T) or 6-fold (Compound IV) higher concentrations (Table 6).

Virus breakthrough was even more delayed with the combination of Compound IV (at 0.1 µg/ml) and TSAO-m³T (at 1.0 or 2.5 µg/ml). Under these experimental conditions, virus was completely suppressed for up to 13 subcultivations (day 46 post infection). Then, when the cultures were further subcultured in the absence of the test compounds for another 10 subcultivations (day 77 post infection), no virus-induced cytopathicity became evident, and the cultures were proven to be viral antigen (p24)-negative. Again, when Compound IV or TSAO-m³T were used at 2.5- to 5-fold higher concentrations as single drug, virus could be suppressed only for 14 to 25 days in cell culture. Thus, the combination of Compound IV with TSAO-m³T resulted in a marked delay or even complete prevention of mutant virus breakthrough which was not obtained if the compounds were used individually at the same or even 2.5- to 5-fold higher concentrations. The triple combinations of Compound IV, TSAO-m³T and BHAP afforded an even more striking effect. When added at lower concentrations, the triple-drug combinations were able to substantially delay (till day 39, day 46, or day 56) or even prevent emergence of resistant virus [no virus breakthrough by day 77 (22th subcultivation)], whereas the highest single-drug concentrations could only prevent virus breakthrough till day 14 to 21 (Table 6). All triple-drug combinations in which Compound IV was combined at 0.1 µg/ml were able to clear the HIV-1-infected CEM cell cultures from virus. Indeed, these cultures became provirus-free as evidenced by PCR, did not produce p24 and grew in the absence of test compounds after the 13th passage at a rate that was indistinguishable from the uninfected CEM cell cultures.

TABLE 6

BREAKTHROUGH OF MUTANT HIV-1 STRAINS IN CEM CELL CULTURES IN
THE DIFFERENT COMBINATIONS OF HIV-1-SPECIFIC RT INHIBITORS AT
VARYING CONCENTRATIONS
(Compound IV, TSAO-m³T and BHAP U90152)

| Compound (concentration: µg/ml) | | Estimation of HIV-1-induced syncytium formation in CEM cells (percentage of control) Days post infection | | | | | | | | | | |
|---|---|---|---|---|---|---|---|---|---|---|---|---|
| | | 4 | 7 | 11 | 14 | 18 | 21 | 25 | 28 | 32 | 35 | 39 |
| BHAP | 0.04 | 0 | 12.5 | 75 | 100 | 100 | 100 | 100 | 100 | 100 | 100 | 100 |
| | 0.10 | 0 | 0 | 0 | 12.5 | 75 | 100 | 100 | 100 | 100 | 100 | 100 |
| | 0.25 | 0 | 0 | 0 | 6.25 | 50 | 100 | 100 | 100 | 100 | 100 | 100 |
| TSAO | 1.0 | 0 | 0 | 0 | 12.5 | 75 | 100 | 100 | 100 | 100 | 100 | 100 |
| | 2.5 | 0 | 0 | 0 | 12.5 | 75 | 100 | 100 | 100 | 100 | 100 | 100 |
| | 5.0 | 0 | 0 | 0 | 12.5 | 75 | 100 | 100 | 100 | 100 | 100 | 100 |
| IV | 0.04 | 0 | 0 | 6.25 | 12.5 | 100 | 100 | 100 | 100 | 100 | 100 | 100 |
| | 0.10 | 0 | 0 | 0 | 6.25 | 6.25 | 87.5 | 87.5 | 100 | 100 | 100 | 100 |
| | 0.25 | 0 | 0 | 0 | 0 | 0 | 3.12 | 19 | 75 | 100 | 100 | 100 |
| IV (0.04) + TSAO (1.0) | | 0 | 0 | 0 | 0 | 3.12 | 12.5 | 50 | 100 | 100 | 100 | 100 |
| IV (0.04) + TSAO (2.5) | | 0 | 0 | 0 | 0 | 0 | 0 | 0 | 15 | 12.5 | 50 | 87.5 |
| IV (0.10) + TSAO (1.0) | | 0 | 0 | 0 | 0 | 0 | 0 | 0 | 0 | 0 | 0 | 0 |
| IV (0.10) + TSAO (2.5) | | 0 | 0 | 0 | 0 | 0 | 0 | 0 | 0 | 0 | 0 | 0 |
| IV (0.04) + TSAO (1.0) + BHAP (0.04) | | 0 | 0 | 0 | 0 | 0 | 0 | 0 | 0 | 0 | 0 | 0 |
| IV (0.04) + TSAO (1.0) + BHAP (0.10) | | 0 | 0 | 0 | 0 | 0 | 0 | 0 | 0 | 0 | 0 | 3.12 |
| IV (0.04) + TSAO (2.5) + BHAP (0.04) | | 0 | 0 | 0 | 0 | 0 | 0 | 0 | 0 | 0 | 0 | 0 |
| IV (0.04) + TSAO (2.5) + BHAP (0.10) | | 0 | 0 | 0 | 0 | 0 | 0 | 0 | 0 | 0 | 0 | 0 |
| IV (0.10) + TSAO (1.0) + BHAP (0.10) | | 0 | 0 | 0 | 0 | 0 | 0 | 0 | 0 | 0 | 0 | 0 |
| IV (0.10) + TSAO (1.0) + BHAP (0.10) | | 0 | 0 | 0 | 0 | 0 | 0 | 0 | 0 | 0 | 0 | 0 |
| IV (0.10) + TSAO (2.5) + BHAP (0.04) | | 0 | 0 | 0 | 0 | 0 | 0 | 0 | 0 | 0 | 0 | 0 |
| IV (0.10) + TSAO (2.5) + BHAP (0.10) | | 0 | 0 | 0 | 0 | 0 | 0 | 0 | 0 | 0 | 0 | 0 |
| CONTROL | | 0 | 100 | 100 | 100 | 100 | 100 | 100 | 100 | 100 | 100 | 100 |

| Compound (concentration: µg/ml) | | Estimation of HIV-1-induced syncytium formation in CEM cells (percentage of control) Days post infection | | | | | | | | | | |
|---|---|---|---|---|---|---|---|---|---|---|---|---|
| | | 42 | 46 | 49 | 53 | 56 | 60 | 64 | 67 | 71 | 74 | 77 |
| BHAP | 0.04 | 100 | 100 | 100 | 100 | 100 | 100 | 100 | 100 | 100 | 100 | 100 |
| | 0.10 | 100 | 100 | 100 | 100 | 100 | 100 | 100 | 100 | 100 | 100 | 100 |
| | 0.25 | 100 | 100 | 100 | 100 | 100 | 100 | 100 | 100 | 100 | 100 | 100 |
| TSAO | 1.0 | 100 | 100 | 100 | 100 | 100 | 100 | 100 | 100 | 100 | 100 | 100 |
| | 2.5 | 100 | 100 | 100 | 100 | 100 | 100 | 100 | 100 | 100 | 100 | 100 |
| | 5.0 | 100 | 100 | 100 | 100 | 100 | 100 | 100 | 100 | 100 | 100 | 100 |
| IV | 0.04 | 100 | 100 | 100 | 100 | 100 | 100 | 100 | 100 | 100 | 100 | 100 |
| | 0.10 | 100 | 100 | 100 | 100 | 100 | 100 | 100 | 100 | 100 | 100 | 100 |

TABLE 6-continued

BREAKTHROUGH OF MUTANT HIV-1 STRAINS IN CEM CELL CULTURES IN
THE DIFFERENT COMBINATIONS OF HIV-1-SPECIFIC RT INHIBITORS AT
VARYING CONCENTRATIONS
(Compound IV, TSAO-m³T and BHAP U90152)

|  | 0.25 | 100 | 100 | 100 | 100 | 100 | 100 | 100 | 100 | 100 | 100 | 100 |
|---|---|---|---|---|---|---|---|---|---|---|---|---|
| IV (0.04) + TSAO (1.0) |  | 100 | 100 | 100 | 100 | 100 | 100 | 100 | 100 | 100 | 100 | 100 |
| IV (0.04) + TSAO (2.5) |  | 100 | 100 | 100 | 100 | 100 | 100 | 100 | 100 | 100 | 100 | 100 |
| IV (0.10) + TSAO (1.0) |  | 0 | 0 | 0 | 0 | 0 | 0 | 0 | 0 | 0 | 0 | 0 |
| IV (0.10) + TSAO (2.5) |  | 0 | 0 | 0 | 0 | 0 | 0 | 0 | 0 | 0 | 0 | 0 |
| IV (0.04) + TSAO (1.0) + BHAP (0.04) |  | 0 | 0 | 0 | 0 | 0 | 0 | 0 | 0 | 0 | 0 | 0 |
| IV (0.04) + TSAO (1.0) + BHAP (0.10) |  | 50 | 75 | 87.5 | 100 | 100 | 100 | 100 | 100 | 100 | 100 | 100 |
| IV (0.04) + TSAO (2.5) + BHAP (0.04) |  | 0 | 0 | 0 | 0 | 0 | 25 | 75 | 75 | 100 | 100 | 100 |
| IV (0.04) + TSAO (2.5) + BHAP (0.10) |  | 0 | 25 | 50 | 62.5 | 87.5 | 100 | 100 | 100 | 100 | 100 | 100 |
| IV (0.10) + TSAO (1.0) + BHAP (0.10) |  | 0 | 0 | 0 | 0 | 0 | 0 | 0 | 0 | 0 | 0 | 0 |
| IV (0.10) + TSAO (1.0) + BHAP (0.10) |  | 0 | 0 | 0 | 0 | 0 | 0 | 0 | 0 | 0 | 0 | 0 |
| IV (0.10) + TSAO (2.5) + BHAP (0.04) |  | 0 | 0 | 0 | 0 | 0 | 0 | 0 | 0 | 0 | 0 | 0 |
| IV (0.10) + TSAO (2.5) + BHAP (0.10) |  | 0 | 0 | 0 | 0 | 0 | 0 | 0 | 0 | 0 | 0 | 0 |
| CONTROL |  | 100 | 100 | 100 | 100 | 100 | 100 | 100 | 100 | 100 | 100 | 100 |

What is claimed is:

1. A composition which comprises an effective amount of:
   a) a first HIV-1-specific nonnucleoside RT inhibitor compound of the formula

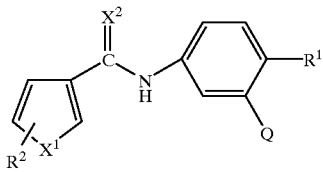

(I)

wherein $X^1$ and $X^2$ are independently O or S;

Q is 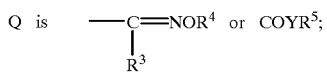 or $COYR^5$;

Y is O or S;

$R^1$ is hydrogen, halogen, $C_1$–$C_4$ alkyl, $C_1$–$C_4$ alkoxy, $C_3$–$C_4$ alkenyloxy, $C_3$–$C_4$ alkynyloxy, mono-, di- or tri-halomethyl, trifluoromethoxy, $C_1$–$C_4$ alkylthio, $C_3$–$C_4$ branched alkylthio, nitro, or cyano;

$R^2$ is hydrogen, $C_1$–$C_4$ alkyl or halogen;

$R^3$ is hydrogen or $C_1$–$C_4$ alkyl;

$R^4$ is $C_3$–$C_6$ alkyl, $C_3$–$C_6$ alkenyl, $C_3$–$C_6$ alkynyl, $C_1$–$C_8$ haloalkyl, $C_1$–$C_8$ alkoxyalkyl, $C_1$–$C_8$ alkylthioalkyl, $C_1$–$C_8$ hydroxyalkyl, $C_1$–$C_8$ acyloxyalkyl, $C_1$–$C_8$ aroyloxyalkyl, $C_1$–$C_8$ carboxyalkyl, $C_1$–$C_8$ alkylcarboxyalkyl, $C_6$–$C_{12}$ arylcarboxyalkyl, $C_1$–$C_8$ aminoalkyl, $C_1$–$C_8$ alkylaminoalkyl, $C_1$–$C_8$ dialkylaminoalkyl, $C_1$–$C_8$ trialkylsilylalkyl, wherein each of the aforementioned alkyl moieties may be straight-chain or branched; $C_3$–$C_8$ cycloalkyl, phenyl, ($C_1$–$C_6$ alkyl)phenyl, $C_7$–$C_{12}$ arylalkyl, $C_7$–$C_{12}$ alkarylalkyl, or heterocycloalkyl, wherein the heterocyclic moiety is morpholinyl, piperidinyl, pyrrolidinyl, piperazinyl, oxiranyl, oxetanyl, furanyl, tetrahydropyranyl or tetrahydrofuranyl; and $R^5$ is
   i) phenyl or $C_3$–$C_7$ cycloalkyl, optionally substituted by one or more $C_1$–$C_4$ alkyl; or
   ii)

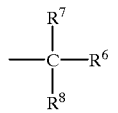

wherein $R^6$ is hydrogen or linear, branched or cyclic, $C_1$–$C_6$ alkyl, $C_1$–$C_6$ hydroxyalkyl, $C_2$–$C_6$ alkenyl, $C_2$–$C_6$ hydroxyalkenyl, $C_2$–$C_6$ alkynyl, $C_2$–$C_6$ hydroxyalkynyl, $C_1$–$C_6$ mono-, di- or tri-haloalkyl or $C_1$–$C_6$ thioalkyl; and $R^7$ and $R^8$ are, independently, hydrogen or, linear, branched or cyclic, $C_1$–$C_6$ alkyl, $C_1$–$C_6$ hydroxyalkyl, $C_2$–$C_6$ alkenyl, $C_2$–$C_6$ hydroxyalkenyl, $C_2$–$C_6$ alkynyl, $C_2$–$C_6$ hydroxyalkynyl, $C_1$–$C_6$ mono-, di- or tri-haloalkyl or $C_1$–$C_6$ thioalkyl; and b) a second HIV-1-specific nonnucleoside RT inhibitor compound which does not select for the same HIV-1 mutant strain or strains selected for by the first HIV-1 RT-specific nonnucleoside inhibitor compound of a).

2. A composition as recited in claim 1 wherein $X^1$ is O and $X^2$ is S.

3. A composition as recited in claim 1 wherein Q is $COYR^5$.

4. A composition as recited in claim 3 wherein Y is O.

5. A composition as recited in claim 1 wherein $R^1$ is halogen.

6. A composition as recited in claim 1 wherein $R^2$ is hydrogen, methyl or ethyl.

7. A composition as recited in claim 1 wherein $R^4$ is $C_3$–$C_6$ alkyl, $C_3$–$C_6$ alkenyl, $C_3$–$C_6$ alkynyl, $C_1$–$C_8$ haloalkyl, or ($C_1$–$C_8$ alkyl)thio($C_1$–$C_8$)alkyl, wherein each of the aforementioned alkyl moieties may be straight-chain or branched; $C_3$–$C_8$ cycloalkyl or phenyl.

8. A composition as recited in claim 1 wherein $R^5$ is
   i) phenyl or $C_3$–$C_7$ cycloalkyl, optionally substituted by one or two methyl; or
   ii)

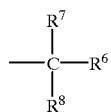

wherein
$R^6$ is hydrogen or linear, branched or cyclic, $C_1$–$C_6$ alkyl, $C_1$–$C_6$ hydroxyalkyl, $C_2$–$C_6$ alkenyl, $C_2$–$C_6$ hydroxyalkenyl, $C_2$–$C_6$ alkynyl, $C_2$–$C_6$ hydroxyalkynyl, $C_1$–$C_6$ mono-, di- or tri-haloalkyl or $C_1$–$C_6$ thioalkyl; and
$R^7$ and $R^8$ are hydrogen or $C_1$–$C_4$ alkyl, linear, branched or cyclic.

9. A composition as recited in claim 8 wherein $R^6$ is linear, branched or cyclic, $C_3$–$C_6$ alkyl, $C_1$–$C_6$ mono-, di- or tri-haloalkyl or $C_1$–$C_6$ thioalkyl; and $R^7$ and $R^8$ are hydrogen.

10. A composition which comprises an effective amount of:
a) an HIV-1 RT inhibitor compound of the formula

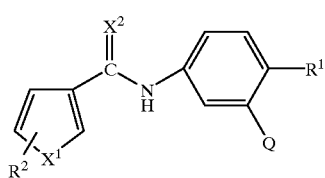

(I)

wherein $X^1$ and $X^2$ are independently O or S;

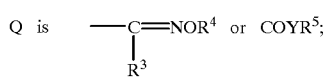

Q is    —C=NOR$^4$ or COYR$^5$;
         |
         $R^3$

Y is O or S;
$R^1$ is hydrogen, halogen, $C_1$–$C_4$ alkyl, $C_1$–$C_4$ alkoxy, $C_3$–$C_4$ alkenyloxy, $C_3$–$C_4$ alkynyloxy, mono-, di- or tri-halomethyl, trifluoromethoxy, $C_1$–$C_4$ alkylthio, $C_3$–$C_4$ branched alkylthio, nitro, or cyano;
$R^2$ is hydrogen, $C_1$–$C_4$ alkyl or halogen;
$R^3$ is hydrogen or $C_1$–$C_4$ alkyl;
$R^4$ is $C_3$–$C_6$ alkyl, $C_3$–$C_6$ alkenyl, $C_3$–$C_6$ alkynyl, $C_1$–$C_8$ haloalkyl, $C_1$–$C_8$ alkoxyalkyl, $C_1$–$C_8$ alkylthioalkyl, $C_1$–$C_8$ hydroxyalkyl, $C_1$–$C_8$ acyloxyalkyl, $C_1$–$C_8$ aroyloxyalkyl, $C_1$–$C_8$ carboxyalkyl, $C_1$–$C_8$ alkylcarboxyalkyl, $C_6$–$C_{12}$ arylcarboxyalkyl, $C_1$–$C_8$ aminoalkyl, $C_1$–$C_8$ alkylaminoalkyl, $C_1$–$C_8$ dialkylaminoalkyl, $C_1$–$C_8$ trialkylsilylalkyl, wherein each of the aforementioned alkyl moieties may be straight-chain or branched; $C_3$–$C_8$ cycloalkyl, phenyl, ($C_1$–$C_6$ alkyl)phenyl, $C_7$–$C_{12}$ arylalkyl, $C_7$–$C_{12}$ alkarylalkyl, or heterocycloalkyl wherein the heterocyclic moiety is morpholinyl, piperidinyl, pyrrolidinyl, piperazinyl, oxiranyl, oxetanyl, furanyl, tetrahydropyranyl or tetrahydrofuranyl; and
$R^5$ is
i) phenyl or $C_3$–$C_7$ cycloalkyl, optionally substituted by one or more $C_1$–$C_4$ alkyl; or
ii)

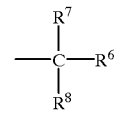

wherein
$R^6$ is hydrogen or linear, branched or cyclic $C_1$–$C_6$ alkyl, $C_1$–$C_6$ hydroxyalkyl, $C_2$–$C_6$ alkenyl, $C_2$–$C_6$ hydroxyalkenyl, $C_2$–$C_6$ alkynyl, $C_2$–$C_6$ hydroxyalkynyl, $C_1$–$C_6$ mono-, di- or tri-haloalkyl or $C_1$–$C_6$ thioalkyl; and
$R^7$ and $R^8$ are, independently, hydrogen or, linear, branched or cyclic, $C_1$–$C_6$ alkyl, $C_1$–$C_6$ hydroxyalkyl, $C_2$–$C_6$ alkenyl, $C_2$–$C_6$ hydroxyalkenyl, $C_2$–$C_6$ alkynyl, $C_2$–$C_6$ hydroxyalkynyl, $C_1$–$C_6$ mono-, di- or tri-haloalkyl or $C_1$–$C_6$ thioalkyl; and b) a second HIV-1 RT inhibitor compound which does not select for the same HIV-1 mutant strain or strains selected for by the first HIV-1-specific RT inhibitor compound of a), of the formula

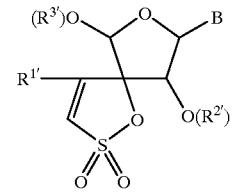

wherein:
B is
i) a pyrimidine of the formula

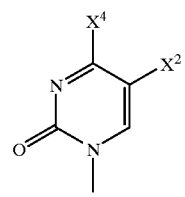 or 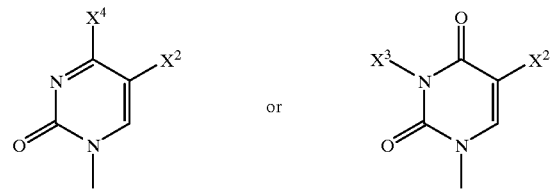

wherein
$X^2$ is a hydrogen, $C_1$–$C_4$ alkyl, $C_2$–$C_4$ alkenyl, $C_2$–$C_4$ alkynyl, halogen, cyano, thiocyano, hydroxymethyl, $C_1$–$C_2$ haloalkyl, nitro or amino;
$X^3$ is hydrogen, $C_1$–$C_4$ alkyl, $C_2$–$C_4$ alkenyl or $C_2$–$C_4$ alkynyl;
$X^4$ is OH, SH, $NH_2$, $NHCH_3$, $N(CH_3)_2$ or $NHCOCH_3$;

ii) a purine of the formula

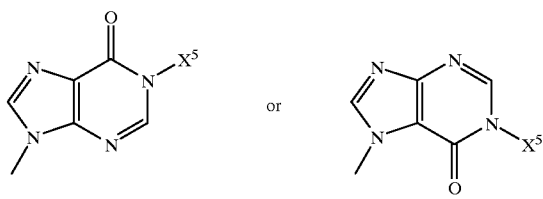

or a purine of the formula

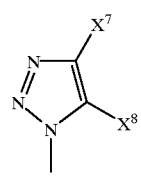

wherein $X^5$ is H or $C_1$–$C_4$ alkyl; and
$X^6$ is H, OH, halogen, $NH_2$, $NHCH_3$ or $N(CH_3)_2$; or
(iii) a triazole of the formula

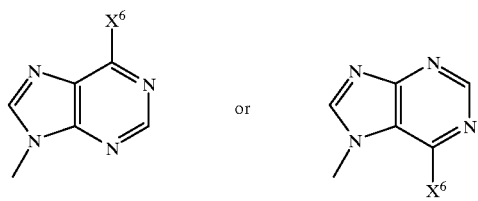

wherein $X^7$ and $X^8$ are each independently hydrogen, $C_1$–$C_4$ alkyl, $C_1$–$C_4$ haloalkyl, trimethylsilyl, acetyl, $C_1$–$C_6$ alkoxycarbonyl, $C_1$–$C_6$ alkylcarbonyl, $CONH_2$, $CONHCH_3$, $CON(CH_3)_2$, $NH_2$, $NHCH_3$ or $N(CH_3)_2$;

$R^1$ is amino, $C_1$–$C_4$ aminoalkyl, $C_2$–$C_4$ aminoalkenyl or $C_2$–$C_4$ aminoalkynyl; and $R^{2'}$ and $R^{3'}$ are each independently, silyl tri-substituted by the same or different, phenyl or $C_1$–$C_4$ linear or branched alkyl.

11. A composition as recited in claim 10 wherein B is
i) a pyrimidine of the formula

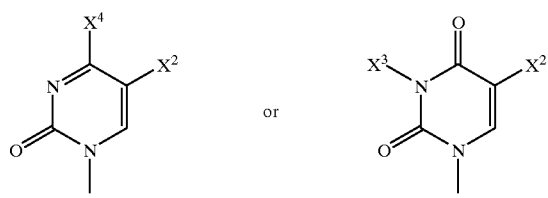

wherein $X^2$ is a hydrogen or $C_1$–$C_4$ alkyl;
$X^3$ is hydrogen or $C_1$–$C_4$ alkyl;
$X^4$ is $NH_2$, $NHCH$, or $N(CH_3)_2$;

ii) a purine of the formula

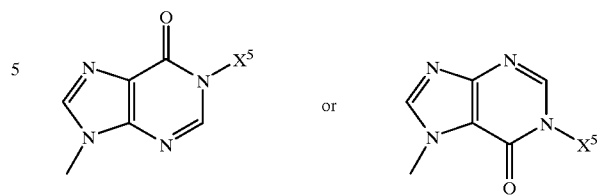

wherein
$X^5$ is $C_1$–$C_4$ alkyl; or
(iii) a triazole of the formula

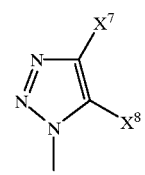

wherein
$X^7$ and $X^8$ are each independently hydrogen, $C_1$–$C_4$ alkyl, $C_1$–$C_4$ haloalkyl, trimethylsilyl, acetyl, $C_1$–$C_6$ alkoxycarbonyl, $C_1$–$C_6$ alkylcarbonyl, $CONH_2$, $CONHCH_3$, $CON(CH_3)_2$, $NH_2$, $NHCH_3$ or $N(CH_3)_2$.

12. A composition as recited in claim 11 wherein B is
i) a pyrimidine of the formula

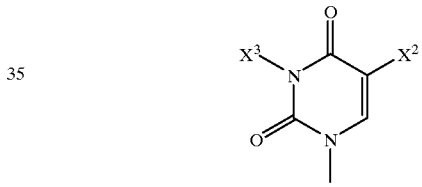

wherein
$X^2$ is a hydrogen or $C_4$–$C_4$ alkyl;
$X^3$ is hydrogen or $C_1$–$C_4$ alkyl;
ii) a purine of the formula

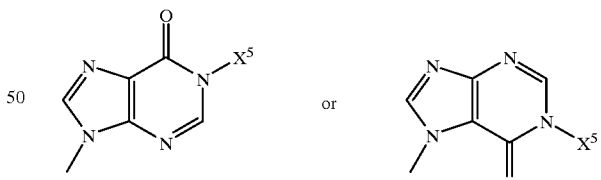

wherein $X^5$ is $C_1$–$C_4$ alkyl; or
(iii) a triazole of the formula

wherein

X⁷ and X⁸ are each independently NH₂, NHCH₃ or N(CH₃)₂.

13. A composition as recited in claim 10 wherein R¹' is amino or C₁–C₄ aminoalkyl.

14. A composition as recited in claim additionally comprising a third HIV RT inhibitor compound which does not select for the same HIV-1 mutant strain or strains as the first HIV-1-specific nonnucleoside RT inhibitor compound or the second HIV-1-specific nonnucleoside RT inhibitor compound.

15. A composition as recited in claim 10 additionally comprising a third HIV RT inhibitor compound which does not select for the same HIV-1 mutant strain or strains as the first HIV-1 RT inhibitor compound or the second HIV-1 RT inhibitor compound.

16. A composition as recited in claim 15 wherein the third HIV RT inhibitor compound is a HIV RT inhibitor which does not discriminate between HIV-1 and HIV-2 RT.

17. A composition as recited in claim 1 which comprises
a) a first HIV-1 RT inhibitor compound of the formula

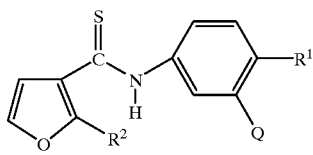

wherein
Q is

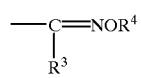

or COYR⁵;
Y is O;
R¹ is hydrogen, halogen, or C₁–C₄ alkyl;
R² is hydrogen or C₁–C₄ alkyl;
R³ is hydrogen or C₁–C₄ alkyl;
R⁴ is C₃–C₆ alkyl, C₃–C₆ alkenyl, C₃–C₆ alkynyl, C₁–C₈ haloalkyl, or (C₁–C₈ alkyl)thio(C₁–C₈)alkyl, wherein each of the aforementioned alkyl moieties may be straight-chain or branched; C₃–C₈ cycloalkyl or phenyl; and
R⁵ is
  i) phenyl or C₃–C₇ cycloalkyl, optionally substituted by one or two methyl; or
  ii)

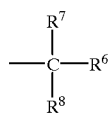

wherein
R⁶ is linear, branched or cyclic, C₁–C₆ alkyl, C₁–C₆ hydroxyalkyl, C₂–C₆ alkenyl, C₂–C₆ hydroxyalkenyl, C₂–C₆ alkynyl, C₂–C₆ hydroxyalkynyl, C₁–C₆ mono-, di- or tri-haloalkyl or C₁–C₆ thioalkyl; and
  R⁷ and R⁸ are hydrogen or C₁–C₄ alkyl, linear, branched or cyclic;

b) a second HIV-1 RT inhibitor compound of the formula

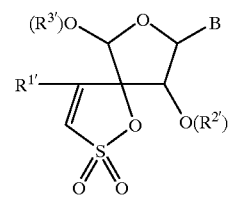

wherein:
B is
  i) a pyrimidine of the formula

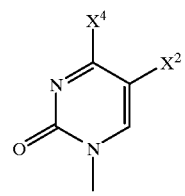 or 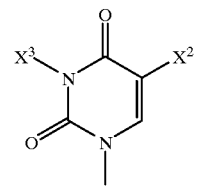

wherein
X² is a hydrogen or C₁–C₄ alkyl;
X³ is hydrogen or C₁–C₄ alkyl;
X⁴ is NH₂, NHCH₃ or N(CH₃)₂;
  ii) a purine of the formula

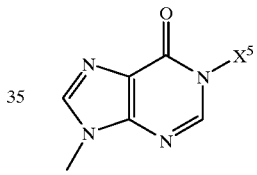 or 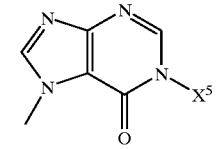

wherein
X⁵ is C₁–C₄ alkyl; or
  (iii) a triazole of the formula

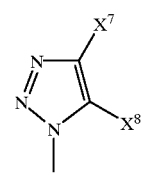

wherein
X⁷ and X⁸ are each independently hydrogen, C₁–C₄ alkyl, C₁–C₄ haloalkyl, trimethylsilyl, acetyl, C₁–C₆ alkoxycarbonyl, C₁–C₆ alkylcarbonyl, CONH₂, CONHCH₃, CON(CH₃)₂, NH₂, NHCH₃ or N(CH₃)₂;
R¹' is amino or C₁–C₄ aminoalkyl; and
R²' and R³' are each independently, silyl tri-substituted by the same or different, phenyl or C₁–C₄ linear or branched alkyl; and
c) optionally, a third HIV RT inhibitor compound which does not select for the same HIV-1 mutant strain or strains selected for by either the first HIV-1 RT inhibitor compound of a) or the second HIV-1 RT inhibitor compound of b).

18. A composition as recited in claim 14 which comprises a) a first HIV-1 RT inhibitor compound of the formula

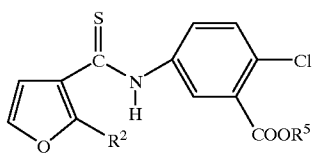

wherein $R^2$ is hydrogen, methyl or ethyl; and
$R^5$ is
   i) phenyl or $C_3$–$C_7$ cycloalkyl; or
   ii)

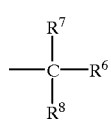

wherein $R^6$ is hydrogen or linear, branched or cyclic, $C_3$–$C_6$ alkyl, $C_1$–$C_6$ mono-, di- or tri-haloalkyl or $C_1$–$C_6$ thioalkyl; and
$R^7$ and $R^8$ are hydrogen;

b) a second HIV-1 RT inhibitor compound of the formula

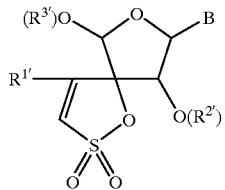

wherein:

B is i) a pyrimidine of the formula

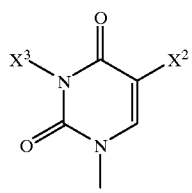

wherein
   $X^2$ is a hydrogen or $C_1$–$C_4$ alkyl;
   $X^3$ is hydrogen or $C_1$–$C_4$ alkyl;
   ii) a purine of the formula

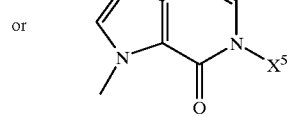

wherein
   $X^5$ is $C_1$–$C_4$ alkyl; or
   (iii) a triazole of the formula wherein
   $X^7$ and $X^8$ are each independently $NH_2$, $NHCH_3$ or $N(CH_3)_2$;
$R^{1'}$ is amino or $C_1$–$C_4$ aminoalkyl; and
$R^{2'}$ and $R^{3'}$ are each independently, silyl tri-substituted by the same or different, phenyl or $C_1$–$C_4$ linear or branched alkyl; and c) optionally, a third HIV RT inhibitor compound which does not select for the same HIV-1 mutant strain or strains selected for by either the first HIV-1 RT inhibitor compound of a) or the second HIV-1 RT inhibitor compound of b).

* * * * *